(12) United States Patent
Holt

(10) Patent No.: US 8,777,485 B2
(45) Date of Patent: Jul. 15, 2014

(54) METHOD AND APPARATUS PERTAINING TO COMPUTED TOMOGRAPHY SCANNING USING A CALIBRATION PHANTOM

(75) Inventor: Kevin M. Holt, Chicago, IL (US)

(73) Assignee: Varian Medical Systems, Inc., Palo Alto, CA (US)

( * ) Notice: Subject to any disclaimer, the term of this patent is extended or adjusted under 35 U.S.C. 154(b) by 653 days.

(21) Appl. No.: 12/890,156

(22) Filed: Sep. 24, 2010

(65) Prior Publication Data

US 2012/0076259 A1 Mar. 29, 2012

(51) Int. Cl.
*G01D 18/00* (2006.01)
*A61B 6/03* (2006.01)
*A61B 6/04* (2006.01)

(52) U.S. Cl.
USPC ............. 378/207; 378/10; 378/18; 250/252.1

(58) Field of Classification Search
USPC ............... 378/10, 18, 57, 163, 207, 208, 209; 250/252.2, 252.1
See application file for complete search history.

(56) References Cited

U.S. PATENT DOCUMENTS

| 4,228,515 | A |   | 10/1980 | Genna et al. |
| 4,233,507 | A | * | 11/1980 | Volz ................... 378/18 |
| 4,305,127 | A |   | 12/1981 | Heuscher |
| 4,613,754 | A | * | 9/1986  | Vinegar et al. ............. 250/252.1 |
| 4,782,502 | A | * | 11/1988 | Schulz ............... 378/18 |
| 4,922,915 | A | * | 5/1990  | Arnold et al. .................. 382/128 |
| 5,012,498 | A | * | 4/1991  | Cuzin et al. ...................... 378/22 |
| 5,023,895 | A | * | 6/1991  | McCroskey et al. .............. 378/4 |
| 5,034,969 | A | * | 7/1991  | Ozaki ............... 378/18 |
| 5,214,578 | A |   | 5/1993  | Cornuejols et al. |
| 5,390,112 | A |   | 2/1995  | Tam |
| 5,442,674 | A |   | 8/1995  | Picard et al. |
| 5,450,461 | A |   | 9/1995  | Hsieh |
| 5,706,324 | A | * | 1/1998  | Wiesent et al. .................... 378/4 |
| 5,786,594 | A |   | 7/1998  | Ito et al. |

(Continued)

FOREIGN PATENT DOCUMENTS

| JP | 2004037267 |    | 2/2004 |
| JP | 2004061256 |    | 2/2004 |
| WO | 2007043974 | A1 | 4/2007 |
| WO | 2007050083 | A1 | 5/2007 |

OTHER PUBLICATIONS

Silver, Michael D., Specification for wACTIS PreProcessing, Bio-Imaging Research, Inc., Sep. 7, 2003-Aug. 11, 2006, 39 pages.

(Continued)

*Primary Examiner* — Allen C. Ho
(74) *Attorney, Agent, or Firm* — Fitch, Even, Tabin & Flannery LLP

(57) ABSTRACT

These various embodiments serve to facilitate improving the accuracy of a computed tomography (CT) process. This can comprise operably coupling at least one calibration phantom to a CT scan table and then, during a CT scan of an object that is disposed on the scan table, also gathering calibration information using that calibration phantom(s). By one approach, this calibration phantom can comprise one or more annular-shaped members. When using a plurality of annular-shaped members, at least some of the annular-shaped members can be disposed concentrically with one another. By one approach, in lieu of the foregoing or in combination therewith, this calibration phantom can comprise one or more pins and/or spherically-shaped members (and/or other shapes of geometric interest). If desired, such spherically-shaped members can be combined with the aforementioned pins.

13 Claims, 3 Drawing Sheets

(56) References Cited

U.S. PATENT DOCUMENTS

| | | | | |
|---|---|---|---|---|
| 5,792,146 | A * | 8/1998 | Cosman | 606/130 |
| 5,822,396 | A * | 10/1998 | Navab et al. | 378/207 |
| 5,835,563 | A * | 11/1998 | Navab et al. | 378/207 |
| 5,951,475 | A * | 9/1999 | Gueziec et al. | 600/425 |
| 6,038,282 | A * | 3/2000 | Wiesent et al. | 378/62 |
| 6,044,132 | A * | 3/2000 | Navab | 378/163 |
| 6,148,058 | A * | 11/2000 | Dobbs | 378/19 |
| 6,243,439 | B1 * | 6/2001 | Arai et al. | 378/20 |
| 6,434,214 | B1 * | 8/2002 | Kawai et al. | 378/4 |
| 6,470,068 | B2 * | 10/2002 | Cheng | 378/20 |
| 6,715,918 | B2 * | 4/2004 | Mitschke et al. | 378/207 |
| 6,739,752 | B2 * | 5/2004 | Sabczynski et al. | 378/207 |
| 6,851,855 | B2 * | 2/2005 | Mitschke et al. | 378/207 |
| 6,909,768 | B2 * | 6/2005 | Takagi et al. | 378/4 |
| 7,006,594 | B2 * | 2/2006 | Chell et al. | 378/18 |
| 7,010,095 | B2 * | 3/2006 | Mitschke et al. | 378/162 |
| 7,016,456 | B2 * | 3/2006 | Basu et al. | 378/18 |
| 7,147,373 | B2 * | 12/2006 | Cho et al. | 378/207 |
| 7,257,190 | B2 * | 8/2007 | Tsujii | 378/62 |
| 7,310,404 | B2 * | 12/2007 | Tashiro et al. | 378/10 |
| 7,510,325 | B2 * | 3/2009 | Endo et al. | 378/207 |
| 7,569,829 | B2 | 8/2009 | Chen et al. | |
| 7,700,909 | B2 | 4/2010 | Holt | |
| 7,715,606 | B2 * | 5/2010 | Jeung et al. | 382/128 |
| 7,729,469 | B2 * | 6/2010 | Kobayashi | 378/10 |
| 7,866,884 | B2 * | 1/2011 | Seto | 378/207 |
| 7,925,326 | B2 * | 4/2011 | Siegel et al. | 600/414 |
| 7,950,849 | B2 * | 5/2011 | Claus et al. | 378/207 |
| 7,967,507 | B2 * | 6/2011 | Levine et al. | 378/207 |
| 8,007,173 | B2 * | 8/2011 | Paidi et al. | 378/207 |
| 8,104,958 | B2 * | 1/2012 | Weiser et al. | 378/207 |
| 2003/0072409 | A1 | 4/2003 | Kaufhold et al. | |
| 2003/0163271 | A1 | 8/2003 | Chell et al. | |
| 2003/0167142 | A1 | 9/2003 | Chell et al. | |
| 2004/0022364 | A1 | 2/2004 | Stierstorfer et al. | |
| 2005/0041771 | A1 | 2/2005 | Kuo-Petravic et al. | |
| 2005/0276375 | A1 | 12/2005 | Urushiya | |
| 2006/0100510 | A1 * | 5/2006 | Klausz | 600/429 |
| 2006/0115054 | A1 | 6/2006 | Yatsenko et al. | |
| 2007/0116183 | A1 | 5/2007 | Ueki et al. | |
| 2007/0172033 | A1 | 7/2007 | Gorges et al. | |
| 2007/0274456 | A1 | 11/2007 | Holt | |
| 2007/0295897 | A1 | 12/2007 | Lyoussi et al. | |
| 2010/0266190 | A1 * | 10/2010 | Zagorchev et al. | 382/132 |
| 2010/0278409 | A1 * | 11/2010 | Wiemker et al. | 382/131 |

OTHER PUBLICATIONS

Press et al., "Numerical Recipes in C, The Art of Scientific Computing," Copyright © Cambridge University Press 1988-1992, Australia, cover page-p. xv (13 pages).

Press et al., "Numerical Recipes in C, The Art of Scientific Computing," Chapter 10: "Minimization or Maximization of Functions;" Copyright © Cambridge University Press 1988-1992, Australia, 62 pages.

Press et al., "Numerical Recipes in C, The Art of Scientific Computing," Chapter 15.4: "General Linear Least Squares," Copyright © Cambridge University Press 1988-1992, Australia, 11 pages.

Silver, Michael D., "Specification for wACTIS CRAY," Bio-Imaging Research, Inc., Apr. 9, 2004-May 23, 2005;17 pages.

Zamyatin et al., "Helical Cone Beam CT with an Asymmetrical Detector," Medical Physics, vol. 32, No. 10, Oct. 2005, pp. 3117-3127.

Silver, Michael D., Specification forwACTIS Backprojection, Bio-Imaging Research, Inc., Oct. 23, 2003-Sep. 15, 2005, 30 pages.

Drawing Sheet—wACTIS Master Geometry Document, Jan. 23, 2004, 1 page.

International Search Report from PCT/US2005/039121, Oct. 12, 2006; 5 pages.

Noo et al., "Analytic Method Based on Identification of Ellipse Parameters for Scanner Calibration in Cone-Beam Tomography," Physics in Medicine and Biology, vol. 45, 2000, pp. 3489-3500.

Bingham et al., "Calibration and Performance Testing for Reconfigurable Computed Tomography Systems," Materials Evaluation, Nov. 2007, 6 pages.

Crawford et al., Reconstruction for fan beam with an angular-dependent displaced center-of-rotation, 1998, Medical Physics,vol. 15, No. 1, pp. 67-71.

Concepcion et al., CT Fan Beam Reconstruction with a Nonstationary Axis of Rotation, Mar. 1992, IEEE Transactions on Medical Imaging, vol. 11, No. 1, pp. 111-116.

Song et al., Development and Evaluation of a MicroCT System for Small Animal Imaging, Nov. 2001, IEEE 2001 Nuclear Science Conference Record, vol. 3, pp. 1600-1604.

Gullberg et al., Estimation of Geometrical parameters for fan beam tomography, 1987, Physics in Medicine and Biology, vol. 32, No. 12, pp. 1581-1594.

Bushberg et al., The Essential Physics of Medical Imaging, 2002, ISBN 0-683-30118-7; 6 pages.

Class Definition for Class 378, X-ray or Gamma Ray Systems or Devices, USPTO Class Definitions; 4 pages.

* cited by examiner

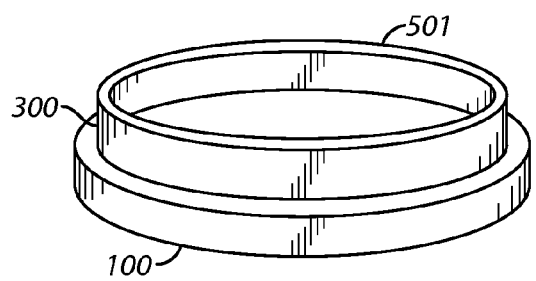
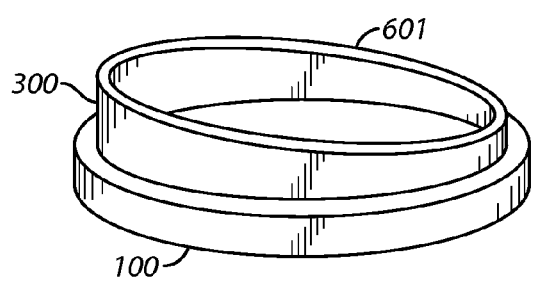
FIG. 5   FIG. 6
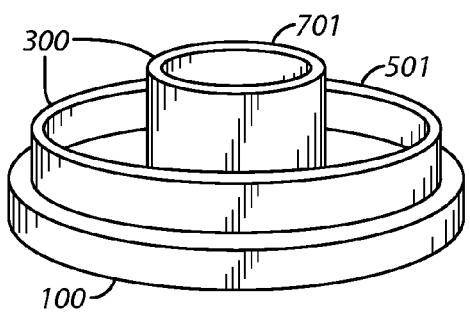
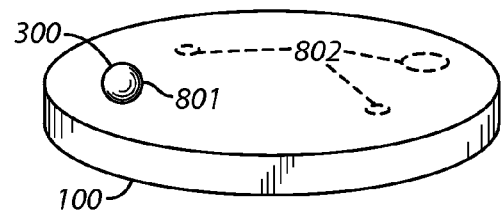
FIG. 7   FIG. 8
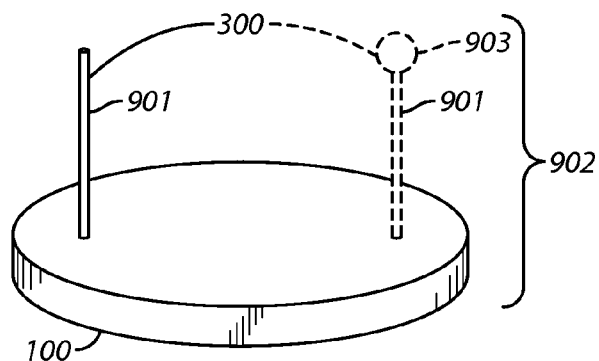
FIG. 9

METHOD AND APPARATUS PERTAINING TO COMPUTED TOMOGRAPHY SCANNING USING A CALIBRATION PHANTOM

RELATED APPLICATION(S)

This application is related to co-owned U.S. Pat. No. 7,922,390 corresponding to U.S. patent application Ser. No. 12/046,337, entitled METHOD AND APPARATUS TO FACILITATE FORMING DETECTOR-LEVEL CALIBRATION INFORMATION FOR A HIGH ENERGY-BASED SCANNER and filed Mar. 11, 2008, which is incorporated by reference in its entirety herein.

This application is related to co-pending and co-owned U.S. Publication No. 2007/0274456 A1 corresponding to U.S. patent application Ser. No. 11/419,793, entitled METHOD AND APPARATUS TO FACILITATE DETERMINATION OF A PARAMETER THAT CORRESPONDS TO A SCANNING GEOMETRY CHARACTERISTIC and filed May 23, 2006, which is incorporated by reference in its entirety herein This application is related to co-owned U.S. Pat. No. 7,700,909, entitled METHOD AND APPARATUS FOR AUTO-CALIBRATION OF A CT SCANNER as issued on Apr. 20, 2010, which is incorporated by reference in its entirety herein.

TECHNICAL FIELD

This invention relates generally to computed tomography (CT) and more particularly to the use of calibration phantoms.

BACKGROUND

Computed tomography comprises a known area of endeavor. CT scanning and processing typically provides a three-dimensional image (or images) of the inside of an object as typically derived from a large series of two-dimensional X-ray images taken around a single axis of rotation (though other energy sources or motion trajectories are also sometimes employed in related processes). In many cases the object rests atop a CT scan table that rotates about this axis of rotation during the scanning process.

Unfortunately, small inconsistencies and/or changes with respect to the various geometries of a CT platform can lead to erroneous processing results. This can include dynamic variations that occur over time. Some technicians use so-called calibration phantoms to compensate for such dynamic variations. Calibration phantoms typically comprise an object having a known shape (such as a pin shape) comprised of a known material.

Calibration phantoms are typically placed or fixed atop the CT scan table to the exclusion of any other object and then scanned like an ordinary object of interest. The corresponding processing platform then uses the known information regarding the calibration phantom to develop corresponding calibration information. The processing platform then uses this calibration information to compensate for detected geometric variations when subsequently scanning objects of interest other than calibration phantoms.

Though a very successful approach when properly utilized, the use of calibration phantoms in this way can contribute to overall delay and/or effective downtime for the CT platform. To avoid such results, technicians may elect to calibrate their equipment less frequently. This, however, can lead to less-accurate scanning results or higher artifact levels. The trade-off seems intractable—achieve greater productivity with less assured accuracy, or achieve greater assured accuracy with reduced productivity.

BRIEF DESCRIPTION OF THE DRAWINGS

The above needs are at least partially met through provision of the method and apparatus pertaining to computed tomography scanning using a calibration phantom described in the following detailed description, particularly when studied in conjunction with the drawings, wherein:

FIG. 5 comprises a bottom perspective view as configured in accordance with various embodiments of the invention;

FIG. 6 comprises a bottom perspective view as configured in accordance with various embodiments of the invention;

FIG. 7 comprises a bottom perspective view as configured in accordance with various embodiments of the invention;

FIG. 8 comprises a bottom perspective view as configured in accordance with various embodiments of the invention;

FIG. 9 comprises a bottom perspective view as configured in accordance with various embodiments of the invention;

Figure 1:
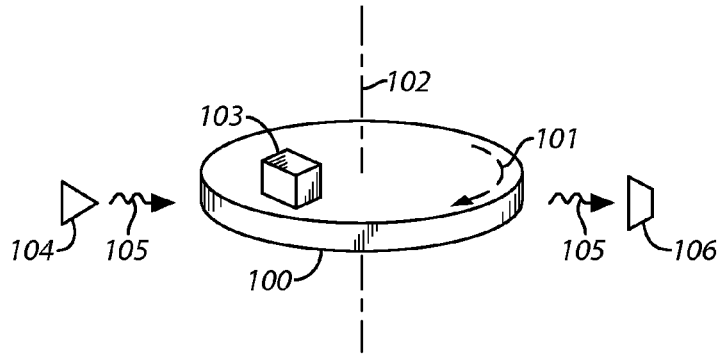
FIG. 1 comprises a schematic view as configured in accordance with the prior art.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, these various embodiments serve to facilitate improving the accuracy of a computed tomography (CT) process. This can comprise operably coupling at least one calibration phantom to a CT scan table and then, during a CT scan of an object that is disposed on the scan table, also gathering calibration information using that calibration phantom(s).

By one approach, this calibration phantom can comprise one or more annular-shaped members. When using a plurality of annular-shaped members, at least some of the annular-shaped members can be disposed concentrically with one another. By one approach, if desired, one or more of the annular-shaped members can have top and bottom planes that are non-parallel with one another.

By one approach, in lieu of the foregoing or in combination therewith, this calibration phantom can comprise one or more pins and/or spherically-shaped members (and/or other shapes of geometric interest). If desired, such spherically-shaped members can be combined with the aforementioned pins. When using a plurality of spherically-shaped members the latter may be substantially similar in size/shape or may be considerably different from one another.

The aforementioned calibration-information gathering step can comprise gathering dimensional calibration information. This dimensional calibration information can comprise, for example, one or more of x-plane dimensional calibration information, y-plane dimensional calibration information, z-plane dimensional calibration information, or warp dimensional calibration information. By another approach, in lieu of the foregoing or in combination therewith, this calibration-information gathering step can comprise the gathering of scanner geometry calibration information using the aforementioned calibration phantom(s). By yet another approach, in lieu of the foregoing or in combination therewith, this calibration-information gathering step can comprise the gathering of signal calibration information using the aforementioned calibration phantom(s).

So configured, the calibration phantom(s) can be left in place even while scanning an object of interest. This is because the object to be scanned and the calibration phantom(s) are separated by a substantially horizontal plane that includes at least the upper surface of the CT scan table. Accordingly, the presence of one will not interfere with the scanning of the other. Accordingly, in a single scanning pass, one can obtain both calibration information as well as imaging data for the object of interest. The calibration information can be processed in accord with ordinary practice to then permit appropriate compensation (as necessary) of the imaging data for the object.

These teachings therefore permit regular calibration of a CT platform without requiring any non-productive calibration-only scans. These teachings are readily applied with existing fielded equipment and hence represent a powerful leveraging opportunity in these regards. It will be further appreciated that these teachings do not require new advances with respect to calibration calculations and/or the processing of scanned images using calibration information.

These and other benefits may become clearer upon making a thorough review and study of the following detailed description. Referring now to the drawings, and in particular to FIG. 1, it may be helpful to begin with a brief description of a typical prior art application setting in these regards. It will be understood that the teachings described herein are not limited to the specifics of this described application setting and that these specifics are provided to assist with a general understanding of these teachings.

A scan table 100 comprises, in this illustrative example, a circular table that rotates (as suggested by the arrow denoted by reference numeral 101 and in response to a given motive force (not shown)) about a central axis of rotation 102. Such scan tables are known in the art and, for the sake of brevity and simplicity, no further elaboration will be provided here in these regards. Such a scan table 100 serves to support an object 103 to be imaged. This object 103 can comprise, for example, a person, an inanimate object, or the like.

A radiation source 104 of choice directs radiation 105 (such as X-ray beams, though other beams can serve, such as proton beams) towards the foregoing and a detector 106 (which typically comprises a detector array comprised of many individual detector elements) then receives the radiation 105 subsequent to the latter's interaction with the object 103 and table 100. The scan table 100, and hence the object 103, rotate to permit different views of the object 103 to be detected. A processing platform (not shown) of choice then gathers that information and utilizes the information to form the desired three-dimensional image of the object 103 including its interior. In a typical application the scan table 100 and object 103 will be rotated a complete 360 degrees in order to capture a corresponding 360 degree view of the object 103.

There are also application settings that make use of slice-direction motion (which for industrial scanning is usually in the vertical direction), either in combination with the foregoing or in lieu thereof. For example, both fan-beam and cone-beam arrangements may employ vertical motion to accommodate, for example, an object that is larger than the area/volume covered by the beam. This may involve moving the scan table 100 up and down and/or moving the source/detector up and down (either in a segregated manner or at the same time).

Figure 2:
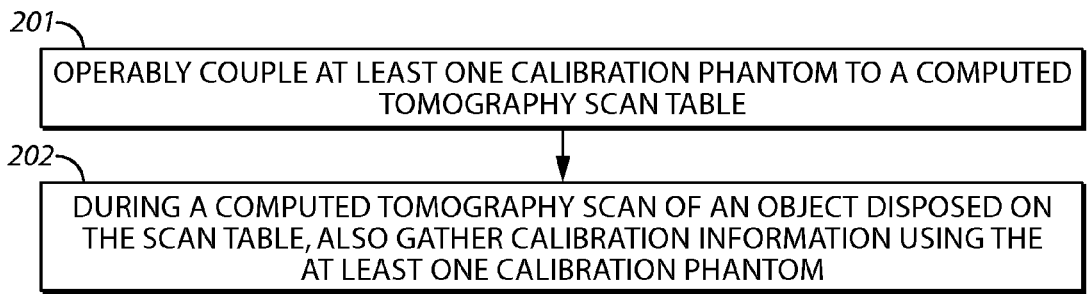
FIG. 2 comprises a flow diagram as configured in accordance with various embodiments of the invention.

Referring now to FIG. 2, an illustrative process 200 to facilitate improving the accuracy of a computed tomography process and that is compatible with many of these teachings will be presented.

This process 200 provides the step 201 of operably coupling at least one calibration phantom to a CT scan table. (As used herein in this context, the expression "operably coupling" means that the one or more calibration phantoms move in lockstep with the scan table when the latter rotates during the course of a CT scan as described above. By one approach, this can comprise physically attaching the calibration phantom to the scan table such that as the latter moves, so moves the former.) By one approach, and in order to avoid any imaging conflicts between the object to be imaged and the calibration phantom(s), the calibration phantom(s) can be attached to the underside of the scanning table such that the object rests above the plane defined by the top of the scanning table while the calibration phantom(s) are disposed below that plane.

Such a calibration phantom will typically be formed of one or more materials (such as tungsten, steel, plastic, or the like) that will absorb at least some of aforementioned radiation. This, in turn, will facilitate identifying the location and boundaries of the calibration phantom in the corresponding resultant images. In addition, the calibration phantom(s) can assume any of a number of useful form factors. Without intending any particular limitations in these regards, a number of possibilities in these regards will now be described.

Figure 3:
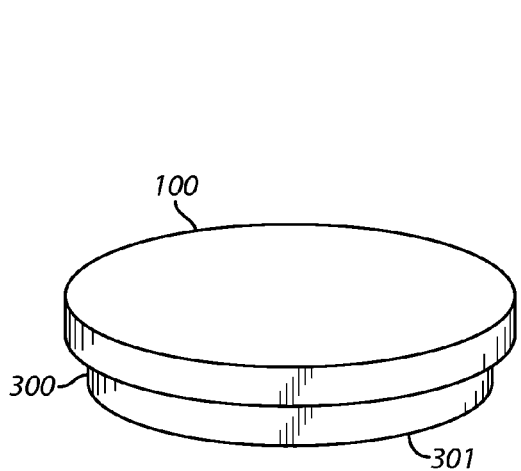
FIG. 3 comprises a top perspective view as configured in accordance with various embodiments of the invention.
Figure 4:
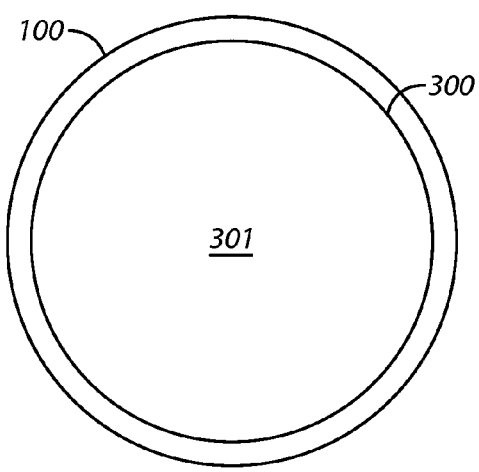
FIG. 4 comprises a bottom plan view as configured in accordance with various embodiments of the invention.

With reference to FIGS. 3 and 4, the calibration phantom 300 can comprise a solid cylinder 301 that connects to the underside of the scan table 100. In this illustrative example, the solid cylinder 301 is concentrically aligned with the scan table 100 and has a lesser diameter. The thickness of the solid cylinder 301 can vary as desired. As examples, this thickness can be about one half the thickness of the scan table 100, or about equal to the thickness of the scan table 100, or about twice the thickness of the scan table 100. Other possibilities are of course available depending upon the needs and/or opportunities that tend to characterize a given application setting.

For many application settings it may be useful in these regards to accommodate the relevant detector pixel height. Generally speaking, it can be helpful to have the phantom no less than one pixel in height with heights of two or more pixels being appropriate in many cases. As one non-limiting, illustrative example in these regards, a typical metal-casting scanner having pixels of from about 0.5 to 1.0 mm in height, the calibration phantom 300 can be about 5 to 20 mm in height. Other possibilities abound however. For example, in a case where the pixel height may only be around 0.01 to 0.05 mm, the calibration phantom 300 height might be around 0.1 to 2.0 mm.

With this in mind, the thickness of the calibration phantom 300 can range (for many application settings of interest) from about 1.0 pixel to around 20.0 pixels (though indeed, in theory, there is no particular upper end limit that specifically applies in these regards). As another non-limiting real-world illustration in these regards, in a metal-castings scanner having a pixel width of from about 0.25 to about 0.6 mm's, the calibration phantom 300 may have a width from about 2.5 mm to 15 mm. In another system having pixels of around 0.01 to 0.05 mm in width, the calibration phantom 300 could instead have a width of around 0.1 mm to 0.5 mm.

Figure 13:
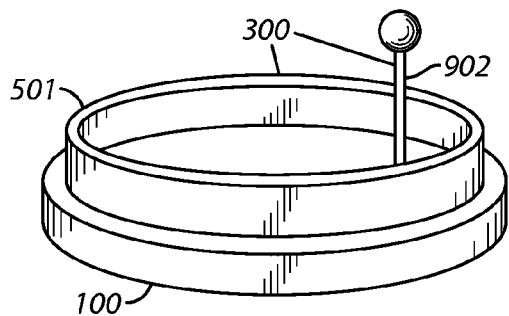
FIG. 13 comprises a bottom perspective view as configured in accordance with various embodiments of the invention.

For many purposes it may serve better if the calibration phantom has the form of an annular-shaped member. FIG. 5 illustrates such an approach (note that FIGS. 5 through 9 as well as FIG. 13 depict the underside of the scan table 100 for the sake of an improved view of the calibration phantom(s)). As before, the height of this annular-shaped member 501 can be as desired, as can the thickness of the wall of the annular-shaped member 501. Also as before, the diameter of the annular-shaped member 501 is less than the diameter of the scan table 100. Generally speaking, for many application settings it may be useful for the diameter of the calibration phantom to be less than the relevant field of view for the corresponding scanning apparatus. By way of illustration in these regards, with a field of view of 200 mm one might employ an annular-shaped member having a diameter of 150 mm while for a field of view of 300 mm one might employ an annular-shaped member having a diameter of 250 mm.

If desired, however, these two elements could share a same diameter. It would also be possible for the annular-shaped member 501 to have a larger diameter than the scan table 100 if desired.

In the illustrative example of FIG. 5, the top edge of the annular-shaped member 501 (that is, the edge that, in this example, contacts the scan table 100) defines a plane that is parallel to a corresponding plane formed by the opposing edge (i.e., the bottom edge, which faces upwardly in FIG. 5) of the annular-shaped member 501. If desired, however, and as suggested by the illustration of FIG. 6, these planes can be non-parallel. Such an approach may be helpful in some application settings as this configuration may yield a greater number of calibration points of interest.

The angle of inclination of this edge 601 as depicted in FIG. 6 is smoothly linear such that this edge 601 of the annular-shaped member 501 all lies within a common plane. If desired, however, this need not be the case. It would be possible for this edge 601 to comprise a smooth but non-linear edge (such as a curved edge).

In fact, these teachings will also accommodate any of a variety of notches, holes, and other discontinuities that wholly or partially disrupt the edge and/or body of the annular-shaped member 501. Generally speaking, such irregularities might serve in a given application setting to provide additional calibration points of interest. Such points, in turn, might contribute to the overall ease of use of the calibration phantom 300 and/or to the overall accuracy of the resultant compensation metrics.

In the examples above, the calibration phantom 300 comprises a single annular-shaped member. These teachings will also accommodate, if desired, using a plurality of annular-shaped members. FIG. 7 presents one such example having a second annular-shaped member 701 disposed concentrically within a first annular-shaped member 501. As one non-limiting illustrative example in these regards, and presuming a scanning system having an adjustable field of view of from around 200 mm to about 300 mm, the inner member could have a diameter of about 150 mm while the outer member could have a diameter of about 250 mm.

As noted, these teachings will accommodate having a plurality of annular-shaped members. Again by way of a non-limiting illustrative example in such regards, this might comprise using five concentrically-disposed annular-shaped members. In such a case, and still only by way of illustration and not by limitation, the inner-most member could have a diameter of 50 mm, with the remaining members having diameters of 100 mm, 150 mm, 200 mm, and 250 mm, respectively. Such an approach would readily accommodate a wide range of adjustable fields of view and would also have the benefit of providing a great number of calibration-relevant data points.

In this example, the second annular-shaped member 701 is taller than the first annular-shaped member 501 and hence extends beyond the vertical boundary of the first annular-shaped member 501. The extent to whether this happens, and by how much, can of course vary from one application setting to another. These teachings will of course accommodate including additional such annular-shaped members as desired, and also will accommodate disposing such annular-shaped members in other than a concentric configuration. This can include disposing the members in other than a nested orientation as shown.

By one approach these annular-shaped members are comprised of a same material. By another approach, if desired, at least some of these annular-shaped members are comprised of different materials from one another. As a simple example in these regards, and referring still to FIG. 7, the first annular-shaped member 501 can be comprised of steel while the second annular-shaped member 701 can be comprised of aluminum.

Curved surfaces often work well for many calibration purposes. The aforementioned annular-shaped members accordingly can serve well in these regards. These teachings will also accommodate using, however, elements having other form factors that nevertheless offer curved edges. Referring now to FIG. 8, by one approach this can comprise using a spherically-shaped member 801 as a calibration phantom 300. This can further comprise using a plurality of spherically-shaped members 802 which may, or may not, share a same size and/or material. When using a plurality of spherically-shaped members 802, the latter can be disposed on the scan table 100 symmetrically with respect to one another or can be non-symmetrically disposed, as desired.

Figure 10:
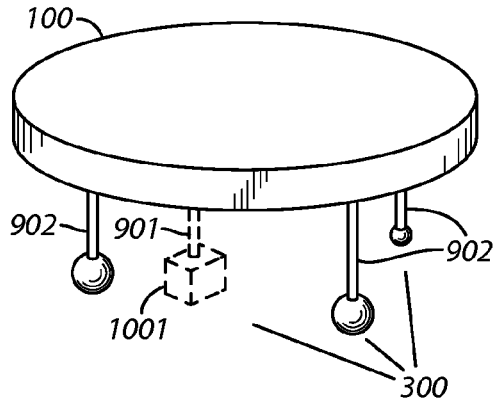
FIG. 10 comprises a top perspective view as configured in accordance with various embodiments of the invention.

With reference to FIG. 9, these teachings will also accommodate using a traditional pin 901 as a calibration phantom if desired. These teachings will also permit, however, combining such a pin 901 with an additional element such as a spherically-shaped member 903 to provide a resultant pin-based-component 902. As shown in FIG. 10, these pin-based-components 902 can have varying lengths and can have additional elements of various sizes. This can even include, if desired, elements of varying form factors as illustrated by the cube 1001 depicted in this figure.

Figure 11:
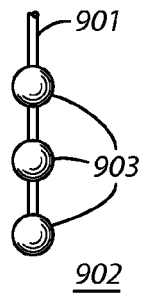
FIG. 11 comprises a front elevational (detail) view as configured in accordance with various embodiments of the invention.
Figure 12:
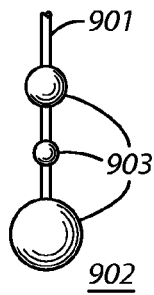
FIG. 12 comprises a front elevational (detail) view as configured in accordance with various embodiments of the invention.

In the examples provided above, the pin-based-component 902 comprises a single element in conjunction with a pin. These teachings will readily accommodate, however, configuring a given pin with a plurality of such elements. As one simple illustrative example in these regards, FIG. 11 depicts a pin 901 having a plurality of equally-sized spherically-shaped members 903 disposed there along. These spherically-shaped members 903 can be equally spaced from one another as suggested by the illustration or can be unequally spaced as desired. As another simple example in these regards, FIG. 12 depicts a pin 901 having a plurality of unequally-sized spherically-shaped members 903 disposed there along. These teachings will of course accommodate using members having shapes other than as a sphere, and will similarly accommodate mixing a variety of differently-shaped members in conjunction with a single common pin 901.

These teachings will accommodate a great variety of other possibilities in these regards and these above examples are not to be taken as an exhaustive listing in these regards. As but one illustrative example in these regards, FIG. 13 depicts a configuration where the calibration phantom 300 comprises both an annularly-shaped member 501 as well as a pin-based component 902, both as described above. One could easily add additional annularly-shaped members and/or additional pin-based components (or, indeed, calibration components of essentially any form factor or size) to such a configuration as desired.

Referring again to FIG. 2, at step 202 this process 200 then provides, during a computed tomography scan of the object 103 that is disposed on the scan table 100, for also gathering calibration information using the at least one calibration phantom 300. This step 202 can occur with, or without, a pre-object calibration scan as desired. Generally speaking, however, as this process 200 permits calibration information to be reliably gathered at the same time as a non-calibration object of interest is being scanned, one may ordinarily expect to be able to successfully omit such a preliminary step. Accordingly, in many application settings this process 200 can match or exceed the accuracy capabilities of calibration-based procedures while also avoiding the diminution of productivity that typically attends calibration-only scans.

This step 202 can accommodate a variety of application settings. By one approach, for example, as when this process 200 serves to facilitate improving dimensional accuracy of a CT process, this step 202 can comprise the gathering of dimensional calibration information via use of the aforementioned calibration phantom(s). This can include any of a variety of dimensional calibration information such as, but not limited to, x-plane dimensional calibration information, y-plane dimensional calibration information, z-plane dimensional calibration information, and/or warp dimensional calibration information. As used herein, the term "warp dimensional" will be understood to refer to any distortion of the image other than a simple scaling in the x, y, or z dimensions. This warp dimensional calibration can be performed in the image space for a reconstructed image, or it can be performed directly on the projection data (before reconstruction). Viewed another way, when this process 200 serves to facilitate improving scanner geometry-based accuracy of a CT process, this step 202 can comprise the gathering of scanner geometry calibration information via use of the aforementioned calibration phantom.

As in dimensional calibration, scanner-geometry calibration might be performed from a reconstructed image, or directly from the projection data. Various approaches are known in the art to facilitate calculating calibration information from the projection data. See, for example, U.S. Pat. No. 7,700,909 entitled METHOD AND APPARATUS FOR AUTO-CALIBRATION OF A CR SCANNER, U.S. Published Patent Application No. 2007/0274456 entitled METHOD AND APPARATUS TO FACILITATE DETERMINATION OF A PARAMETER THAT CORRESPONDS TO A SCANNING GEOMETRY CHARACTERISTIC, and U.S. Pat. No. 7,922,390 corresponding to U.S. Published Patent Application No. 2008/0240365 entitled METHOD AND APPARATUS TO FACILITATE FORMING DETECTOR-LEVEL CALIBRATION INFORMATION FOR A HIGH ENERGY-BASED SCANNER, the contents of which are fully incorporated herein by this reference.

Of course, these teachings will also accommodate the gathering of dimensional calibration information as well as (or even in lieu of gathering dimensional calibration information) scanner geometry calibration information or signal calibration information pursuant to this step 202 if desired. (As used herein, this reference to "signal calibration information" will be understood to refer to operational-performance information regarding, for example, detectors (such as electronic non-linearities, X-ray-based non-linearities, crosstalk, lag, and so forth) or source characteristics.)

Figure 14:
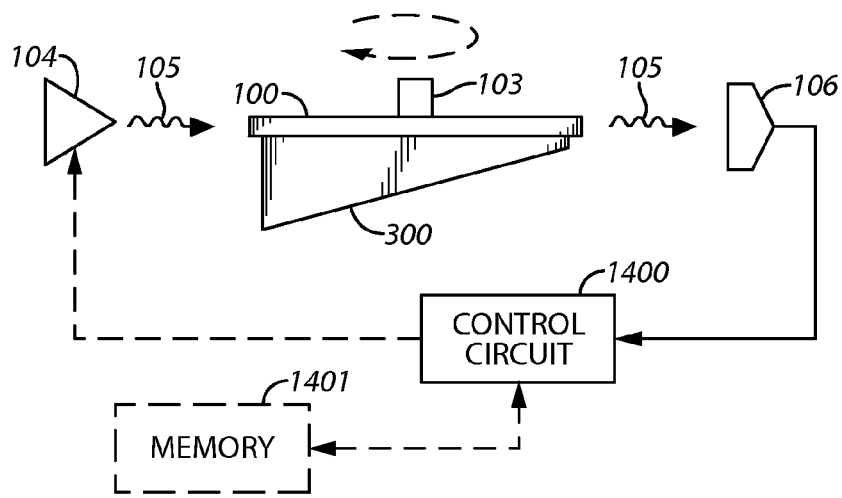
FIG. 14 comprises a schematic view as configured in accordance with various embodiments of the invention.

Referring now to FIG. 14, in this illustrative example, a control circuit 1400 serves to gather the aforementioned calibration information via the detector(s) 106 as gleaned via use of the calibration phantom 300 of choice (where here, the calibration phantom 300 has the form factor described earlier with respect to FIG. 6). Such a control circuit 1400 can comprise a fixed-purpose hard-wired platform or can comprise a partially or wholly programmable platform. All of these architectural options are well known and understood in the art and require no further description here. When the control circuit 1400 comprises an at least partially programmable platform, the control circuit 1400 can be configured, via corresponding programming, to carry out one or more of the steps, actions, and/or functions described herein including step 202 of the described process 200.

If desired, this control circuit 1400 can be operably coupled to a memory 1401. This memory 1401 can serve to store the aforementioned programming and/or the gathered calibration data as desired. It will be understood that this memory 1401 can comprise an integral part of the control circuit 1400 if desired, or can be physically discrete if desired. It will also be understood that this memory 1401 can be local (such that the memory 1401 and control circuit 1400, for example, share a common chassis, power supply, and/or housing) or can be remote (as when the memory physically resides in another facility or building apart from the control circuit 1400 and is accessed via an appropriate network such as the Internet) as desired.

So configured, a CT scanning platform can essentially gain the benefits of calibration via the use of calibration phantoms without suffering the productivity downtime that such use ordinarily entails. This, in turn, can lead to overall reduced operating costs. This can also lead to reduced delays for both technicians and patients. These teachings can be readily applied to and utilized with existing platforms if desired to thereby improve the scan-to-scan accuracy and/or productivity of such existing platforms.

These teachings can also be beneficially applied in application settings where the object being scanned can itself cause calibration issues. For example, when the object being scanned is particularly heavy, the table may tilt or recede in response. By employing these teachings to permit real-time calibration while scanning such an object, the calibration issues presented by such a scenario are essentially avoided.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

As one illustrative example in these regards, it was noted above that these teachings can be employed in an application setting where there is relative slice-direction motion between the table and the scanner. In such a case, when the calibration phantom(s) falls within the beam (for example, when a single cone beam contains both the object to be scanned and the calibration phantom) one can obtain the described calibration information without any additional scanning. When the calibration phantom does not fall within the beam, then one could modify these teachings to make a slice-direction move to position the beam over the phantom to permit some additional scanning.

Though this will require additional scanning time, such incremental time will often be small when compared to prior art practices. Typically there is a large overhead to scanning anything—often a number of overhead steps are required which may include positioning the object, opening and closing the shield door, sounding a safety alarm, waiting a few seconds for safety reasons, turning on the X-rays, and/or permitting the source to stabilize before scanning. The described approach will avoid such collateral temporal overhead even in an application setting that requires some additional scanning for calibration purposes.

As another illustrative example in these regards, some fan-beam scans may take very long (such as 10-24 hours) to build up the image slice by slice. In such an application setting one could provide for an automated calibration scan every, say, 45 minutes during such a process. This would assure, in an automated manner, that the calibration information is never older than the selected calibration-scan period. This, in turn, could prove valuable in settings where, for example, the temperature may be shifting over the long scan time frames involved.

We claim:

1. A method to facilitate improving accuracy of a computed tomography process, comprising:
   operably coupling at least one calibration phantom to a computed tomography scan table by at least one of:
      attaching at least one calibration phantom comprising at least one annular-shaped member to the computed tomography scan table; and
      operably coupling at least one calibration phantom below an upper surface of the computed tomography scan table; and
   during a computed tomography scan of an object disposed on the computed tomography scan table while the computed tomography scan table rotates, also gathering calibration information using the at least one calibration phantom.

2. The method of claim 1, wherein operably coupling at least one calibration phantom to a computed tomography scan table comprises operably coupling a plurality of calibration phantoms to a computed tomography scan table.

3. The method of claim 1, wherein operably coupling at least one calibration phantom to a computed tomography scan table comprises operably coupling at least one calibration phantom comprising at least one spherically-shaped member to the computed tomography scan table.

4. The method of claim 3, wherein operably coupling at least one calibration phantom comprising at least one spherically-shaped member to the computed tomography scan table comprises coupling a pin to the computed tomography scan table, wherein the pin has the at least one spherically-shaped member disposed thereon.

5. The method of claim 4, wherein the at least one spherically-shaped member comprises a plurality of spherically-shaped members.

6. The method of claim 1, wherein:
   the method to facilitate improving accuracy of a computed tomography process comprises a method of improving dimensional accuracy of a computed tomography process; and
   gathering calibration information using the at least one calibration phantom comprises gathering dimensional calibration information using the at least one calibration phantom.

7. The method of claim 6, wherein gathering dimensional calibration information using the at least one calibration phantom comprises gathering dimensional calibration information regarding at least one of:
   x-plane dimensional calibration information;
   y-plane dimensional calibration information;
   z-plane dimensional calibration information;
   warp dimensional calibration information.

8. The method of claim 1, wherein:
   the method to facilitate improving accuracy of a computed tomography process comprises a method of improving scanner geometry-based accuracy of a computed tomography process; and
   gathering calibration information using the at least one calibration phantom comprises gathering scanner geometry calibration information using the at least one calibration phantom.

9. The method of claim 1, wherein:
   the method to facilitate improving accuracy of a computed tomography process comprises a method of improving signal accuracy of a computed tomography process; and
   gathering calibration information using the at least one calibration phantom comprises gathering signal calibration information using the at least one calibration phantom.

10. The method of claim 1, wherein gathering calibration information using the at least one calibration phantom comprises gathering at least two of dimensional calibration information, signal calibration information, and scanner geometry calibration information using the at least one calibration phantom.

11. A method to facilitate improving accuracy of a computed tomography process, comprising:
   operably coupling at least one calibration phantom to a computed tomography scan table by attaching the at least one calibration phantom comprising at least one annular-shaped member to the computed tomography scan table; and
   during a computed tomography scan of an object disposed on the computed tomography scan table, also gathering calibration information using the at least one calibration phantom.

12. The method of claim 11, wherein attaching the at least one calibration phantom comprising at least one annular-shaped member to the computed tomography scan table comprises attaching a plurality of annular-shaped members to the computed tomography scan table.

13. A method to facilitate improving accuracy of a computed tomography process, comprising:

operably coupling at least one calibration phantom to a computed tomography scan table by coupling the at least one calibration phantom below an upper surface of the computed tomography scan table; and during a computed tomography scan of an object disposed on the computed tomography scan table, also gathering calibration information representing dynamic variations to various geometries of a computed tomography platform as corresponds to the computed tomography process using the at least one calibration phantom.

* * * * *